(12) United States Patent
Kim et al.

(10) Patent No.: US 9,637,701 B2
(45) Date of Patent: May 2, 2017

(54) ESTOLIDE COMPOUND CONTAINING KETONE FUNCTIONAL GROUP AND METHOD FOR PREPARING THE SAME

(71) Applicants: SK Innovation Co., Ltd., Seoul (KR); SK Lubricants Co., Ltd., Seoul (KR)

(72) Inventors: Yong Woo Kim, Daejeon (KR); Hee Jung Jeon, Daejeon (KR); Wan Seop Kwon, Daejeon (KR); Hak Mook Kim, Daejeon (KR); Jin Hee Ok, Daejeon (KR)

(73) Assignees: SK Innovation Co., Ltd., Seoul (KR); SK Lubricants Co., Ltd., Seoul (KR)

( * ) Notice: Subject to any disclaimer, the term of this patent is extended or adjusted under 35 U.S.C. 154(b) by 116 days.

(21) Appl. No.: 14/792,959

(22) Filed: Jul. 7, 2015

(65) Prior Publication Data

US 2016/0009631 A1 Jan. 14, 2016

(30) Foreign Application Priority Data

Jul. 8, 2014 (KR) ........................ 10-2014-0084970

(51) Int. Cl.
*C10M 129/72* (2006.01)
*C07C 69/28* (2006.01)
(Continued)

(52) U.S. Cl.
CPC ........... *C10M 129/72* (2013.01); *C07C 45/48* (2013.01); *C07C 51/36* (2013.01); *C07C 51/44* (2013.01);
(Continued)

(58) Field of Classification Search
CPC .............. C10M 129/72; C10M 105/38; C10M 2207/2835; C10N 2220/022; C10N 2220/023; C10N 2230/02; C10N 2270/00; C07C 45/48; C07C 51/36; C07C 51/44; C07C 67/04; C07C 69/28; C11C 3/123
(Continued)

(56) References Cited

U.S. PATENT DOCUMENTS 8,450,256 B2 5/2013 Bredsguard
2012/0172609 A1 7/2012 Bredsguard et al.
(Continued)

FOREIGN PATENT DOCUMENTS

FR 885865 9/1943

OTHER PUBLICATIONS

TRC110 Product Specification, Twin Rivers Technologies, Nov. 2012, http://www.twinriverstechnologies.com/products/whole_cut_acids.html.
(Continued)

*Primary Examiner* — James Goloboy
(74) *Attorney, Agent, or Firm* — The Webb Law Firm

(57) ABSTRACT

A method for preparing a ketone group-containing estolide compound and a ketone group-containing estolide compound prepared thereby are disclosed. The method for preparing a ketone group-containing estolide compound includes converting biomass fat into a fatty acid; separating the fatty acid into a C16 saturated fatty acid and a C18 unsaturated fatty acid; increasing an amount of oleic acid through partial hydrogenation of the C18 unsaturated fatty acid; synthesizing a C35 ketone through ketonization of the oleic acid; and performing estolide bonding by capping the C16 saturated fatty acid onto the C35 ketone.

11 Claims, 4 Drawing Sheets

(51) Int. Cl.
  *C07C 67/04*   (2006.01)
  *C07C 45/48*   (2006.01)
  *C07C 51/36*   (2006.01)
  *C07C 51/44*   (2006.01)
  *C11C 3/12*    (2006.01)
  *C10M 105/38*  (2006.01)

(52) U.S. Cl.
  CPC .............. *C07C 67/04* (2013.01); *C07C 69/28* (2013.01); *C10M 105/38* (2013.01); *C11C 3/123* (2013.01); *C10M 2207/2835* (2013.01); *C10N 2220/022* (2013.01); *C10N 2220/023* (2013.01); *C10N 2230/02* (2013.01); *C10N 2270/00* (2013.01)

(58) Field of Classification Search
  USPC ........................................................ 508/497
  See application file for complete search history.

(56) References Cited

U.S. PATENT DOCUMENTS

| | | |
|---|---|---|
| 2012/0322897 A1 | 12/2012 | Bredsguard |
| 2014/0012023 A1 | 1/2014 | Thompson et al. |

OTHER PUBLICATIONS

Isbell, Chemistry and Physical Properties of Estolides, United States Department of Agriculture Research Service, National Center for Agriculture Utilization Research, 2011, pp. 8-20.

Cermak, S., et al., Physical properties of saturated estolides and their 2-ethylhexyl esters, Industrial Crops and Products, an International Journal, (2002), 119-127, 16.

ESTOLIDE COMPOUND CONTAINING KETONE FUNCTIONAL GROUP AND METHOD FOR PREPARING THE SAME

CROSS-REFERENCE TO RELATED APPLICATION

This application claims priority to and the benefit of Korean Patent Application No. 10-2014-0084970, filed on Jul. 8, 2014 in the Korean Intellectual Property Office, the entire disclosure of which is incorporated herein by reference.

FIELD OF THE INVENTION

The present invention relates to a ketone group-containing estolide compound and a method for preparing the same.

DESCRIPTION OF THE RELATED ART

To prepare an environmentally friendly lubricating oil which exhibits high biodegradability and is free from toxic substances such as S, N, aromatics and heavy metals, a technique for preparing a biomass-derived lubricating oil is proposed.

Recently, estolides are a focus of attention as a biomass-derived environmentally friendly lubricating oil. Materials in which an unsaturated double bond in a hydrocarbon is crosslinked with a carboxyl group are collectively referred to as estolides. Estolides can be naturally derived from castor bean or lesquerella derived vegetable oils. It was known in the art by Penoyer et al. in 1954 that estolides could be prepared by simple synthesis, whereby a possibility of producing estolides as a novel product was suggested.

Although it was recognized from the beginning that there was a possibility of applying estolides as a lubricating oil (Group V, ester base oil) due to structural properties thereof, since triglyceride-derived estolides, which were proposed in the initial stage, did not secure sufficient oxidative stability despite excellent pour point thereof, triglyceride-derived estolides were unsuitable for use as a lubricating oil.

In Chemistry and physical properties of estolide (Isbell, 2011), a 4-step process composed of (1) de-esterification, (2) estolide synthesis, (3) esterification and (4) hydrogenation is disclosed as a process for preparing an estolide. De-esterification is a process of converting triglycerides, which make up the majority of biomass fat, into a fatty acid; estolide synthesis is a process of converting an unsaturated fatty acid into an estolide; esterification is a process of stabilizing the estolide through change into an ester by reacting a carboxyl group present in the estolide with alcohols; and hydrogenation is a process of improving oxidative stability of the estolide by removing an unsaturated double bond present in the estolide.

The prepared estolide exhibits properties of a high quality lubricating base oil that exhibits higher viscosity index, oxidative stability and thermal stability than typical petroleum-based Group I, Group II and Group III base oils, and has a great merit as a lubricating oil in that the estolide can be made into a high-viscosity lubricating base oil based on 100 vis.

However, existing methods for preparing an estolide have fundamental problems as follows.

The first problem is dependency on oleic acid. In initial stages of estolide research, search into preparing an estolide from a triglyceride itself and then using the prepared estolide as a lubricating base oil was carried out. However, since the estolide exhibited poor low-temperature stability when the triglyceride was directly used, the estolide was unsuitable for use as a lubricating base oil. On the other hand, oleic acid was selectively used as a raw material for preparing the estolide, whereby the problem of low-temperature stability of the estolide was significantly reduced while improving other properties of the estolide. However, it could be seen that dependency on oleic acid was significantly increased in the preparation of the estolide. Supply of biomass-derived oleic acid is inherently limited. For example, an amount of oleic acid contained in crude palm oil (CPO) is no more than about 52% by weight (wt %). Therefore, only the content of oleic acid in the biomass fat is used in the preparation of the estolide, and the amount of oleic acid is no more than about 50% in the biomass fat. In addition, there is a problem in that use of the remaining fatty acids excluding oleic acid should be considered.

The second problem is that alcohol is necessary for esterification. Since a fatty acid group is present in the estolide due to estolide reaction and thus can cause various problems such as material instability, corrosiveness, and the like, the estolide must be made into another stable form. In most cases, the estolide is made into an ester form which exhibits high stability and can provide volume gain. Existing estolides are also stabilized in the form of an ester through reaction of an acid group with alcohol. In other words, for reaction stability, it can also be understood that alcohol is necessary. Since alcohol is not created during reaction, there is a problem in that alcohol must be introduced from the outside.

The third problem is that hydrofinishing is necessary. In a typical process for preparing an estolide, hydrofinishing is performed to remove an unsaturated double bond derived from biomass fat. Since the unsaturated double bond can cause deterioration in oxidative stability, it is necessary to remove the unsaturated double bond through hydrogenation. In an existing reaction for preparing estolide, the unsaturated double bond in an estolide structure is also removed by hydrofinishing. However, there are problems in that hydrofinishing is performed by hydrogenation under conditions of high temperature and high pressure and is not economically feasible due to high price of hydrogen.

The fourth problem is that the unsaturated double bond remains in the existing estolide even though the reaction for removing the unsaturated double bond is applied through hydrogenation. Fundamentally, since a lubricating oil can suffer from side reaction such as discoloration due to bonding of the unsaturated double bond to oxygen in air, increased corrosiveness due to increased hygroscopicity, and the like when the unsaturated double bond is present in the molecular structure of the lubricating oil, the remaining unsaturated double bond is generally completely removed through hydrogenation. However, since an ester bond of the estolide can be partially broken during reaction for completely removing the remaining unsaturated double bond, selective removal of the unsaturated double bond is performed under conditions that the ester bond is maintained. For this reason, the unsaturated double bond is not completely removed. Although the estolide has a low iodine value of less than 10, the unsaturated double bond can remain in the estolide.

The fifth problem is that an existing estolide has an ester group exhibiting low steric hindrance. Esterification has a merit in that structural stability unique to an ester and volume gain due to alcohol can be obtained. However, the ester group exhibits relatively higher stability than other functional groups, and cannot be thought absolutely stable. The ester group can be irreversibly converted into a fatty acid depending on reaction conditions, and, in this case, there can be a serious problem of engine corrosion. In fact, in the case of FAME which is in an ester form and is first generation biodiesel, or an ester base oil which is a Group V base oil, engine corrosion caused by a fatty acid created due to the broken ester group has been reported. To overcome these problems, other forms of diesel or anti-corrosion additives are used together.

SUMMARY OF THE INVENTION

It is one aspect of the present invention to provide a ketone group-containing estolide compound exhibiting excellent low-temperature stability and oxidative stability.

It is another aspect of the present invention to provide a ketone group-containing estolide compound which includes an ester group exhibiting high steric hindrance and is free from an unsaturated bond.

It is a further aspect of the present invention to provide a method for preparing a ketone group-containing estolide compound, which can improve processability and economic efficiency while minimizing dependency on oleic acid in preparation of the estolide compound by increasing the content of oleic acid.

It is yet another aspect of the present invention to provide a method for preparing a ketone group-containing estolide compound, which does not require use of alcohols.

It is yet another aspect of the present invention to provide a method for preparing a ketone group-containing estolide compound, which does not require separate hydrofinishing.

One aspect of the present invention relates to a method for preparing a ketone group-containing estolide compound, which includes: converting biomass fat into a fatty acid; separating the fatty acid into a $C_{16}$ saturated fatty acid and a $C_{18}$ unsaturated fatty acid; increasing an amount of oleic acid through partial hydrogenation of the $C_{18}$ unsaturated fatty acid; synthesizing a $C_{35}$ ketone through ketonization of the oleic acid; and performing estolide bonding by capping the $C_{16}$ saturated fatty acid onto the $C_{35}$ ketone.

The $C_{16}$ saturated fatty acid may be palmitic acid, and the $C_{18}$ unsaturated fatty acid may include oleic acid, linoleic acid and linolenic acid.

Partial hydrogenation may be performed at a reaction temperature of about 160° C. to about 180° C. and at a reaction pressure of about 20 bar to about 40 bar in the presence of a supported catalyst in which a NiMo, CoMo or Mo metal is supported on a water resistant carrier.

The water resistant carrier may be $ZrO_2$ or $TiO_2$.

The $C_{18}$ unsaturated fatty acid may include about 90% or more of oleic acid through partial hydrogenation.

Ketonization may be performed by introducing the oleic acid into a fixed bed reactor in the presence of a $Mn_2O_3$ or $TiO_2$ catalyst or a supported catalyst in which zirconium dioxide or thorium dioxide is supported on alumina, followed by reaction at a temperature of about 200° C. to about 600° C. and at a pressure of about 1 psi to about 200 psi.

Performing estolide bonding may include performing reaction by introducing the $C_{35}$ ketone, the $C_{16}$ saturated fatty acid and sulfuric acid or perchloric acid having a purity of about 90% or more into a batch reactor.

In performing estolide bonding, the C35 ketone and the C16 saturated fatty acid may be introduced in a molar ratio of about 1:0.1 to about 1:10.

Another aspect of the present invention relates to a ketone group-containing estolide compound represented by Formula 1.

[Formula 1]

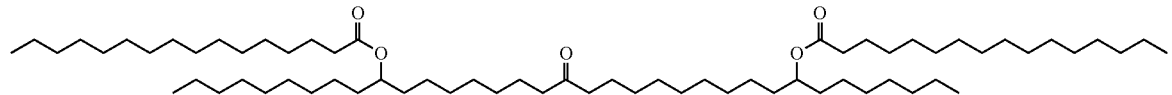

A further aspect of the present invention relates to a lubricating oil including the ketone group-containing estolide compound represented by Formula 1 as set forth above.

The lubricating oil may have a pour point of about −45° C. to about −25° C. and a viscosity index of about 140 to about 180.

DETAILED DESCRIPTION OF THE INVENTION

Method for Preparing Ketone Group-Containing Estolide Compound

Figure 1:
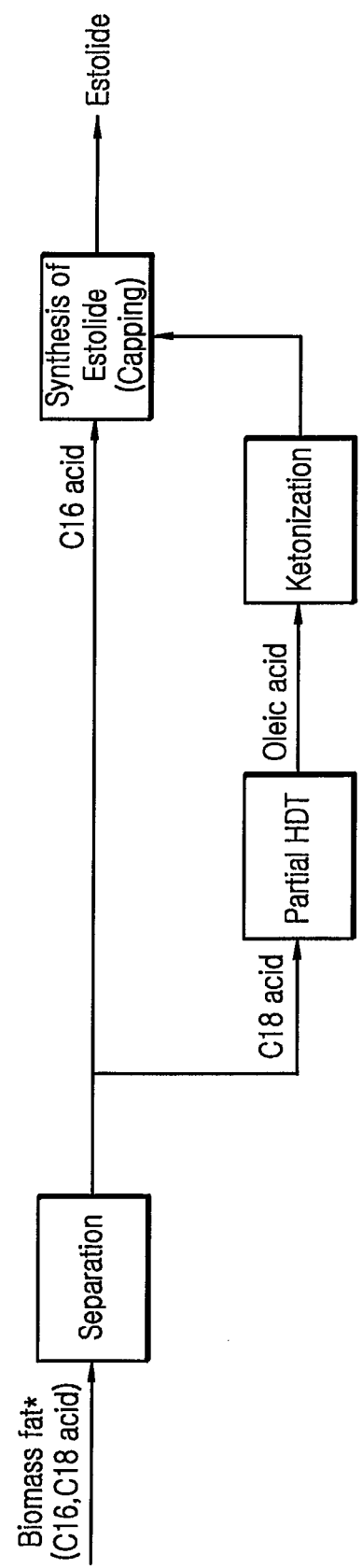
FIG. 1 is a flowchart schematically showing a method for preparing a ketone group-containing estolide compound according to one embodiment of the present invention.
Figure 2:
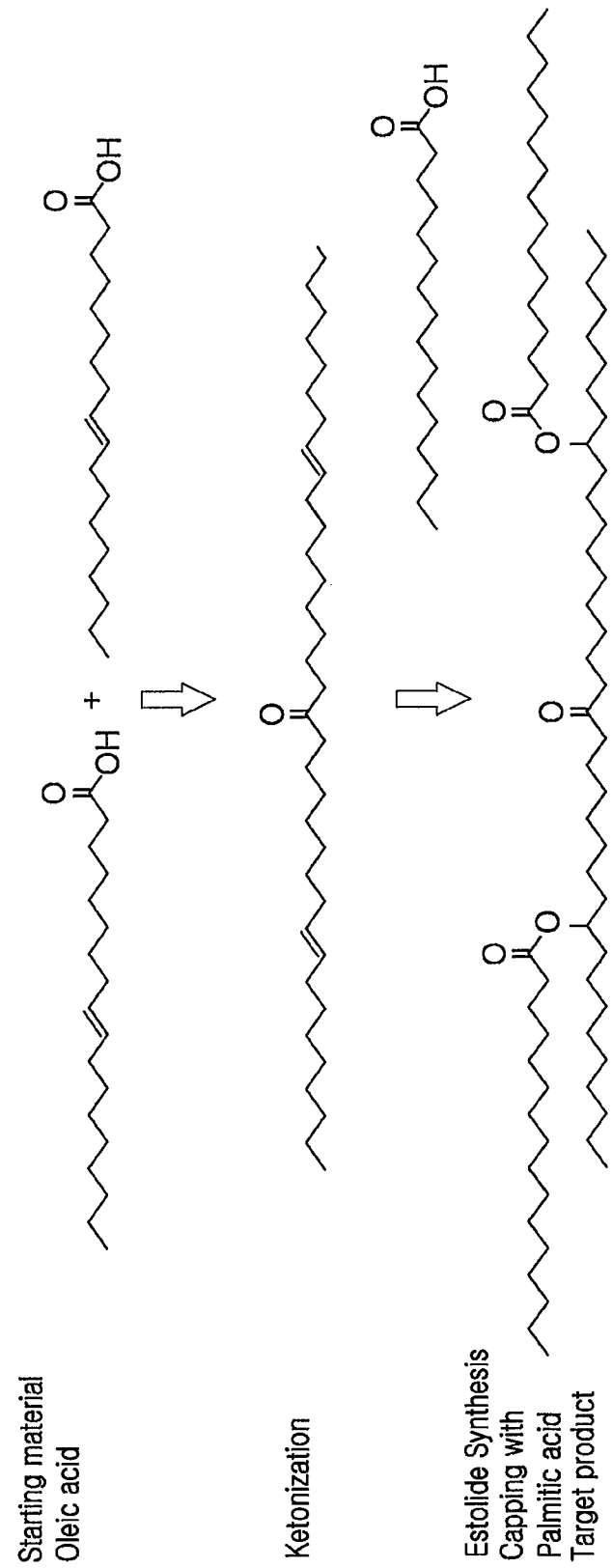
FIG. 2 shows a reaction mechanism of a ketone group-containing estolide compound according to one embodiment of the present invention.

FIG. 1 is a flowchart schematically showing a method for preparing a ketone group-containing estolide compound according to one embodiment of the present invention, and FIG. 2 is a flowchart showing stages of chemical reaction for preparation of a ketone group-containing estolide compound according to one embodiment of the present invention. Referring to FIGS. 1 and 2, each of the stages will be described in detail hereinafter.

According to one embodiment, a method for preparing a ketone group-containing estolide compound includes: converting biomass fat into a fatty acid (S10); separating the fatty acid into a C16 saturated fatty acid and a C18 unsaturated fatty acid (S20); increasing an amount of oleic acid through partial hydrogenation of the C18 unsaturated fatty acid (S30); synthesizing a C35 ketone through ketonization of the oleic acid (S40); and performing estolide bonding by capping the C16 saturated fatty acid onto the C35 ketone (S50).

As generally known in the art, operation S10 of converting biomass fat into a fatty acid may be performed by extracting a triglyceride from the biomass using a strong acid, a strong base, high-temperature steam and the like, followed by converting the triglyceride into a fatty acid through hydrolysis of an ester bond of the triglyceride.

Since the fatty acid derived from the biomass fat includes various saturated fatty acids and unsaturated fatty acids, operation S20 of separating the fatty acid into a C16 saturated fatty acid and a C18 unsaturated fatty acid is performed. For example, fatty acids derived from crude palm oil may include myristic acid, palmitic acid, oleic acid, linoleic acid, linolenic acid, monoglycerides, and diglycerides. As such, since such various fatty acids have different boiling points, a desired fatty acid may be selectively extracted and separated through fractional distillation.

Therefore, the biomass-derived fatty acid may be separated and extracted into the C16 saturated fatty acid (b.p. 300° C. to 355° C.) and the C18 unsaturated fatty acid (b.p. 355° C. to 380° C.) through fractional distillation. The C16 saturated fatty acid may be palmitic acid and the C18 unsaturated fatty acid may include oleic acid, linoleic acid and linolenic acid.

Since a target material of the C18 unsaturated fatty acid used in ketonization described below is oleic acid, linoleic acid and linolenic acid can be directly used in ketonization only after conversion into oleic acid by reducing the number of unsaturated bonds.

Operation S30 of increasing an amount of oleic acid through partial hydrogenation of the C18 unsaturated fatty acid relates to a process of converting linoleic acid (C18:2), linolenic acid (C18:3) or the like of the biomass fat into oleic acid (C18:1).

A catalyst used in partial hydrogenation is a supported catalyst in which NiMo, CoMo, or Mo is supported on a water resistant carrier.

Partial hydrogenation is performed under conditions of a temperature of about 160° C. to about 180° C. and a pressure of about 20 bar to about 40 bar rather than under conditions of a high temperature of 200° C. or more and a high pressure of 40 bar or more, which correspond to typical conditions for hydrogenation. If reaction is performed at a high temperature of 180° C. or more and a high pressure of 20 bar or more, the C18 unsaturated fatty acid can be converted into stearic acid (C18:0) since all unsaturated double bonds are completely removed, or in severer cases, there can occur side reaction in which C15 and C17 linear paraffin is created due to decarboxylation.

For this reason, in order to control the reaction such that only one unsaturated double bond is present by partial saturation of olefins of the biomass fat, which have two or more unsaturated double bonds, the reaction is performed under the limited conditions as set forth above. Even though only some of the olefins having two or more unsaturated double bonds are converted into the olefins having one unsaturated double bond under the limited conditions as set forth above, since all of the olefins having two or more unsaturated double bonds are subjected to partial saturation by recycling, suppression of side reaction is a more important issue than reaction yield.

In addition, the conditions as set forth above differ from typical conditions for hydrogenation in terms of characteristics of biomass. Biomass includes an extremely high amount of oxygen as compared with crude oil. When oxygen is removed through hydrogenation, oxygen is removed in the form of $H_2O$ by reaction with hydrogen and thus causes an active metal and a carrier of the catalyst to dissolve, thereby causing a problem of serious catalyst deactivation. Therefore, when biomass is subjected to hydrogenation, catalyst deactivation due to water created as a by-product can be extremely serious.

According to the present invention, the water resistant carrier, such as $ZrO_2$, $TiO_2$ and the like, is used, whereby the problem of catalyst deactivation due to such catalyst leaching can be overcome.

The C18 unsaturated fatty acid includes about 90% or more of oleic acid through partial hydrogenation.

Operation S40 of synthesizing a C35 ketone through ketonization of the oleic acid may be performed, for example, in a fixed bed reactor into which a $Mn_2O_3$ or $TiO_2$ catalyst or a supported catalyst obtained by supporting zirconium dioxide or thorium dioxide on alumina is introduced.

When the oleic acid is injected into the fixed bed reactor, it is advantageous in terms of ease of operation that a mixed solution prepared by missing the oleic acid with a solvent is injected. The solvent may be light paraffin such as n-heptane, and the oleic acid and the solvent may be mixed in a weight ratio of about 1:0.1 to about 1:10.

Ketonization may be performed at a temperature of about 200° C. to about 600° C. and in a relatively wide pressure range, for example, from about 1 psi to about 200 psi.

Operation S50 of performing estolide bonding by capping the C16 saturated fatty acid onto the C35 ketone is performed to secure stability of a chemical structure by removing an unsaturated bond of the C35 ketone.

The C35 ketone synthesized by ketonization in operation S40 has two unsaturated bonds. Palmitic acid, which is the C16 saturated fatty acid separated in operation S20, is capped onto positions of the unsaturated bonds, thereby forming an estolide bond.

Estolide bonding may be performed by reacting the C35 ketone and palmitic acid with high-purity sulfuric acid, perchloric acid or the like in a batch reactor.

It is desirable that the sulfuric acid have a high purity of about 90% or more. If the sulfuric acid has low purity, since there is a drawback of significant reduction in reaction activity, attention should be paid to the purity of sulfuric acid.

Estolide bonding may be performed at a temperature of about 25° C. to about 80° C. and at a pressure of about 0.1 bar to about 10 bar.

In estolide bonding, the C35 ketone and the C16 saturated fatty acid are advantageously introduced in a molar ratio of about 1:0.1 to about 1:10 to reduce the remaining amount of the biomass.

Ketone Group-Containing Estolide Compound

A ketone group-containing estolide compound, which is prepared by the method as set forth above, may be represented by Formula 1.

[Formula 1]

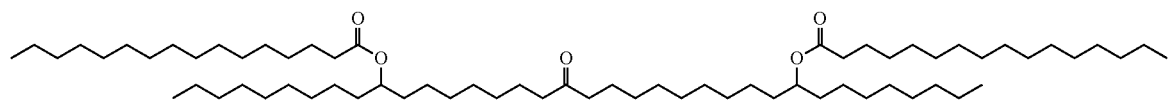

The ketone group-containing estolide compound represented by Formula 1 has merits as an environmentally friendly lubricating oil, for example, high biodegradability and high viscosity index, and exhibits outstanding low-temperature stability and oxidative stability.

Typical ester lubes exhibit relatively low steric hindrance and thus can be readily converted into a fatty acid through collapse of a chemical structure thereof, thereby causing a problem of corrosion. Conversely, since the estolide compound represented by Formula 1 includes an ester group having high steric hindrance, conversion of the estolide compound into acid of an ester can be prevented.

According to one embodiment, a ketone group-containing estolide compound has a pour point of about −45° C. to about −20° C. and a viscosity index of about 140 to about 180, and thus exhibits relatively high viscosity index as compared with pour point thereof.

Hereinafter, the present invention will be described in more detail with reference to some examples. However, it should be noted that these examples are provided for illustration only and are not to be construed in any way as limiting the present invention.

Examples

Figure 3:
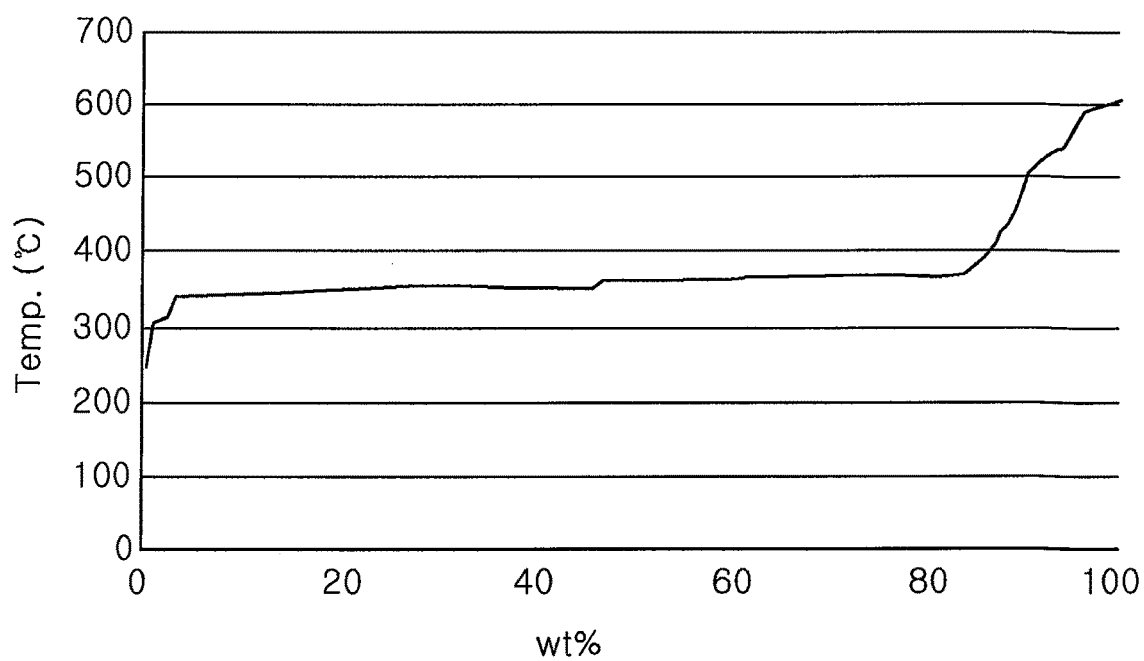
FIG. 3 is a graph depicting an analysis result (SimDist pattern) of a PFAD specimen of Example.

A. Separation of Fatty Acid 2 kg of a palm fatty acid distillate (PFAD) specimen was separated into fatty acids at each of reaction temperatures using a TBP cutting apparatus. From analysis results (SimDist) of the PFAD specimen shown in FIG. 3, it could be confirmed that the PFAD specimen included components present in amounts as listed in Table 1. The PFAD specimen was cut based on the reaction temperatures, that is, 300° C., 355° C. and 380° C., thereby obtaining fatty acids in amounts as listed in Table 2, respectively.

TABLE 1

| Fatty acid | Amount of component of PFAD (wt %) |
| --- | --- |
| Myristic acid (C14:0) | 3 |
| Palmitic acid (C16:0) | 43 |
| Oleic acid (C18:1), Linoleic acid (C18:2), Linolenic acid (C18:3) | 38 |
| Mono-, di-glyceride | 16 |
| Total | 100 |

TABLE 2

| Fatty acid | Boiling point (b.p.) | Amount of each fatty acid separated and obtained (g) |
| --- | --- | --- |
| Myristic acid (C14:0) | 300° C. or less | 56 |
| Palmitic acid (C16:0) | 300° C.~355° C. | 881 |
| Oleic acid (C18:1), Linoleic acid (C18:2), Linolenic acid (C18:3) | 355° C.~380° C. | 742 |
| Mono-, di-glyceride | 380° C. or more | 289 |
| Total | — | 1968 |

B. Partial Hydrogenation for Improvement in Yield of Oleic Acid 742 g of $C_{18}$ fatty acids (C18:1, C18:2, C18:3) obtained in separation of the fatty acids was subjected to partial hydrogenation in the presence of a $NiMo/ZrO_2$ catalyst, thereby converting linoleic acid (C18:2) and linolenic acid (C18:3) into oleic acid (C18:1).

From results of GC-MS analysis, it could be confirmed that linoleic acid and linolenic acid were converted into oleic acid with high selectivity, as shown in Table 3.

TABLE 3

| | Change in amount before and after partial hydrogenation (wt %) | |
| --- | --- | --- |
| Fatty acid | Before | After |
| Oleic acid (C18:1) | 80.3 | 93.9 |
| Linoleic acid (C18:2) | 17.9 | 5.9 |
| Linolenic acid (C18:3) | 1.8 | 0.2 |

After partial hydrogenation, products in Table 3 were introduced into a 500 cc flask, followed by fractional distillation by connecting the flask to a fractional distillation apparatus (Spaltrohr HMS 300C, Fischer technology Co., Ltd.), thereby finally obtaining 682 g of oleic acid.

C. Ketonization: Preparation of Oleic Acid-Derived C35 Ketone 6 g of a powdered $Mn_2O_3$ catalyst was introduced into a fixed bed reactor having an internal diameter of 1 inch, followed by filling upper and lower sides of the catalyst layer with beads. A thermocouple was placed at the center of the catalyst layer in the reactor, followed by connecting the fixed bed reactor to a reaction system.

To remove moisture and impurities physically adsorbed onto an outside of the catalyst layer, the reactor was heated to 120° C. at a rate of 1° C./min at atmospheric pressure at a nitrogen ($N_2$) flow rate of 200 sccm, followed by maintaining the reactor at 120° C. for 2 hours. After completion of pretreatment, the reactor was heated to 350° C. at a rate of 1° C./min at 5 bar at a nitrogen ($N_2$) flow rate of 200 sccm, followed by maintaining the reactor at 350° C. for 30 minutes. Next, a solution in which oleic acid and a solvent (n-heptane) were mixed in a weight ratio of 1:1 was injected into the reactor at a flow rate of 0.13 sccm. Sampling was performed every 6 hours, and a sample after 2 days was taken as a representative sample.

Figure 4:
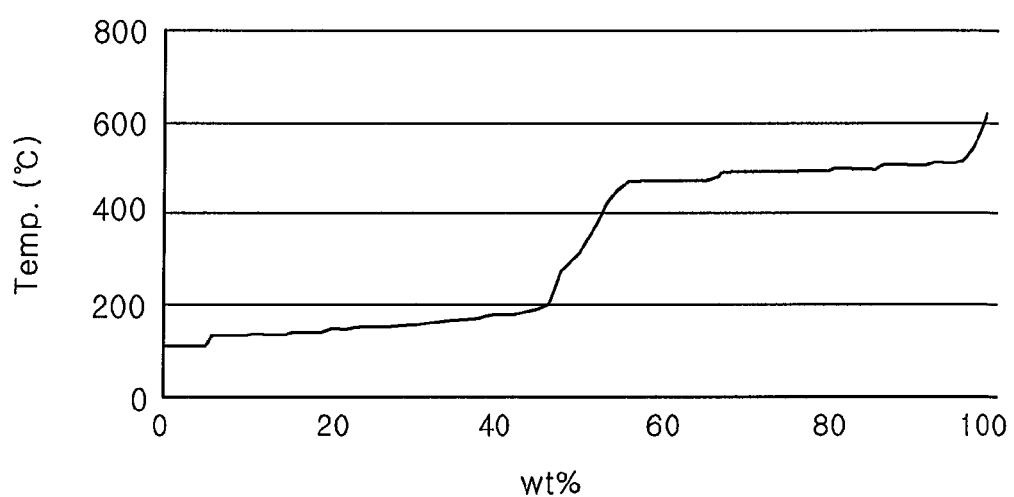
FIG. 4 is a graph depicting an analysis result (SimDist pattern) of a reaction product through ketonization of oleic acid of Example.

FIG. 4 is a graph depicting results of SimDist pattern analysis of the sample. Considering that oleic acid has a boiling point (b.p.) of 360° C., it can be confirmed from FIG. 4 that, after ketonization, the oleic acid was completely converted into a C35 ketone near at 500° C. without side reaction.

D. Preparation of Estolide Compound Through Capping of C16 Fatty Acid 117 g of the $C_{35}$ ketone obtained in operation C, 125 g of palmitic acid which was the $C_{16}$ fatty acid obtained in operation A and 5.8 g of 70% purity perchloric acid were introduced into a 500 cc flask, which in turn was connected to a fractional distillation apparatus (Spaltrohr HMS 300C, Fischer technology Co., Ltd.). Next, the fractional distillation apparatus was heated to 60° C., followed by reducing the pressure of the fractional distillation apparatus to 10 torr, and then maintained for 24 hours while slowly stirring the components. The resulting material was introduced into a 2 L beaker, followed by quenching with a mixed solution of KOH/ethanol/DI-water (3.4 g/100 cc/900 cc) while stirring the resulting material. After confirming by pH measurement that remaining acid was not present in the mixed solution, the mixed solution was left until the temperature of the mixed solution decreased. Next, the mixed solution was introduced into a separatory funnel and settled, followed by selectively removing a water layer after the water layer and an organic layer were separated. The separated organic layer was introduced again into the fractional distillation apparatus (Spaltrohr HMS 300C, Fischer technology Co., Ltd.), and cut at 550° C., thereby removing unreacted material. 129 g of the unreacted material was separated, and 101 g of ketone group-containing estolide compound was secured.

The ketone group-containing estolide compound was evaluated as to properties as a lubricating oil, and results are shown in Table 4.

TABLE 4

| Viscosity (40° C.) | Viscosity (100° C.) | Viscosity index (VI) | Pour point (PP) | Iodine value |
|---|---|---|---|---|
| 18.8 Cst | 135.1 Cst | 157 | −35° C. | 0.04 cg/g |

As shown in Table 4, the ketone group-containing estolide compound prepared in Example exhibited high lubricating-oil properties in terms of VI and PP, and did not have remaining unsaturated double bonds due to the significantly low iodine value thereof.

Since the ketone group-containing estolide compound according to the present invention contains an ester group exhibiting high steric hindrance and does not have unsaturated bonds, the ketone group-containing estolide compound exhibits excellent low-temperature stability and oxidative stability. In addition; the method according to the present invention minimizes dependency on oleic acid upon preparation of the estolide compound by increasing the amount of oleic acid, and provides excellent processability and economic feasibility by eliminating use of alcohols.

What is claimed is:

1. A method for preparing a ketone group-containing estolide compound, comprising:

converting biomass fat into a fatty acid;
separating the fatty acid into a C16 saturated fatty acid and a C18 unsaturated fatty acid;
increasing an amount of oleic acid through partial hydrogenation of the $C_{18}$ unsaturated fatty acid;
synthesizing a C35 ketone through ketonization of the oleic acid; and
performing estolide bonding by capping the C16 saturated fatty acid onto the C35 ketone.

2. The method according to claim 1, wherein the C16 saturated fatty acid is palmitic acid, and the C18 unsaturated fatty acid comprises oleic acid, linoleic acid and linolenic acid.

3. The method according to claim 1, wherein partial hydrogenation is performed at a reaction temperature of about 160° C. to about 180° C. and at a reaction pressure of about 20 bar to about 40 bar in the presence of a supported catalyst in which NiMo, CoMo or Mo is supported on a water resistant carrier.

4. The method according to claim 3, wherein the water resistant carrier is $ZrO_2$ or $TiO_2$.

5. The method according to claim 1, wherein the C18 unsaturated fatty acid comprises about 90% or more of oleic acid through partial hydrogenation.

6. The method according to claim 1, wherein ketonization is performed by introducing the oleic acid into a fixed bed reactor in the presence of a $Mn_2O_3$ or $TiO_2$ catalyst or a supported catalyst in which zirconium dioxide or thorium dioxide is supported on alumina, followed by reaction at a temperature of about 200° C. to about 600° C. and at a pressure of about 1 psi to about 200 psi.

7. The method according to claim 1, wherein performing estolide bonding comprises performing reaction by introducing the C35 ketone, the C16 saturated fatty acid and sulfuric acid or perchloric acid having a purity of about 90% or more into a batch reactor.

8. The method according to claim 1, wherein, in performing estolide bonding, the C35 ketone and the C16 saturated fatty acid are introduced in a molar ratio of about 1:0.1 to about 1:10.

9. A ketone group-containing estolide compound represented by Formula 1.

[Formula 1]

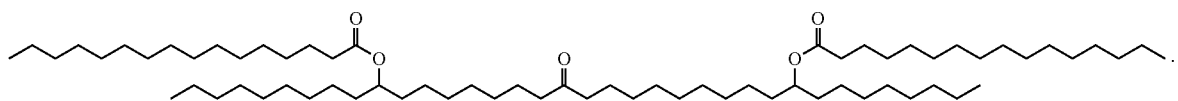

10. A lubricating oil comprising the ketone group-containing estolide compound according to claim 9.

11. The lubricating oil according to claim 10, wherein the lubricating oil has a pour point of about −45° C. to about −25° C. and a viscosity index of about 140 to about 180.

* * * * *